United States Patent
Tollens et al.

(10) Patent No.: US 8,483,553 B2
(45) Date of Patent: *Jul. 9, 2013

(54) VOLATILE EMITTER WITH REDUCED SURFACE DEPOSITION AND IMPROVED SCENT NOTICEABILITY

(75) Inventors: Fernando Ray Tollens, Cincinnati, OH (US); James Robert Tinlin, Cincinnati, OH (US); Arthur Hampton Neergaard, Cincinnati, OH (US); William Paul Mahoney, III, Liberty Township, OH (US); Steven Louis Diersing, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1 day.

This patent is subject to a terminal disclaimer.

(21) Appl. No.: 13/206,699

(22) Filed: Aug. 10, 2011

(65) Prior Publication Data

US 2011/0290911 A1 Dec. 1, 2011

Related U.S. Application Data

(63) Continuation of application No. 12/123,704, filed on May 20, 2008, now Pat. No. 8,135,265.

(51) Int. Cl.
*F24F 6/08* (2006.01)

(52) U.S. Cl.
USPC ............ 392/395; 392/386; 392/394; 392/391

(58) Field of Classification Search
USPC ......... 392/386–406; 239/34–60; 261/75–107; 432/120–213
See application file for complete search history.

(56) References Cited

U.S. PATENT DOCUMENTS

| | | | |
|---|---|---|---|
| 5,518,179 A | 5/1996 | Humberstone et al. | |
| 5,657,926 A | 8/1997 | Toda | |
| 6,752,327 B2 | 6/2004 | Martens, III et al. | |
| 6,859,615 B2 | 2/2005 | Yip et al. | |
| 7,499,632 B2 * | 3/2009 | Granger et al. | 392/386 |
| 7,722,807 B2 * | 5/2010 | Keller et al. | 422/5 |
| 7,744,833 B2 * | 6/2010 | Varanasi et al. | 422/306 |
| 7,845,213 B2 * | 12/2010 | Varanasi et al. | 73/64.52 |
| 2009/0289127 A1 | 11/2009 | Tollens et al. | |

FOREIGN PATENT DOCUMENTS

| | | |
|---|---|---|
| EP | 0 897 755 A2 | 2/1999 |
| EP | 00 923 957 A1 | 6/1999 |
| EP | 1 792 662 A1 | 6/2007 |
| WO | WO 2007/062698 A1 | 6/2007 |

OTHER PUBLICATIONS

PCT International Search Report, 4 pages, Mailed Aug. 5, 2009.

* cited by examiner

*Primary Examiner* — Thor Campbell
(74) *Attorney, Agent, or Firm* — Amy I Ahn-Roll

(57) ABSTRACT

A device for emitting volatile compositions comprising a capillary element, a channel in fluid communication with the capillary element, an emitting orifice having a forward tilt from about +5 degrees to less than about +90 degrees, and a decoupled piezoelectric actuator for emitting the volatile composition through the emitting orifice. In some embodiments, the device is a plug-in air freshener and reduces surface deposition and improves scent noticeability through improved containment of perfumes during the rest period.

18 Claims, 5 Drawing Sheets

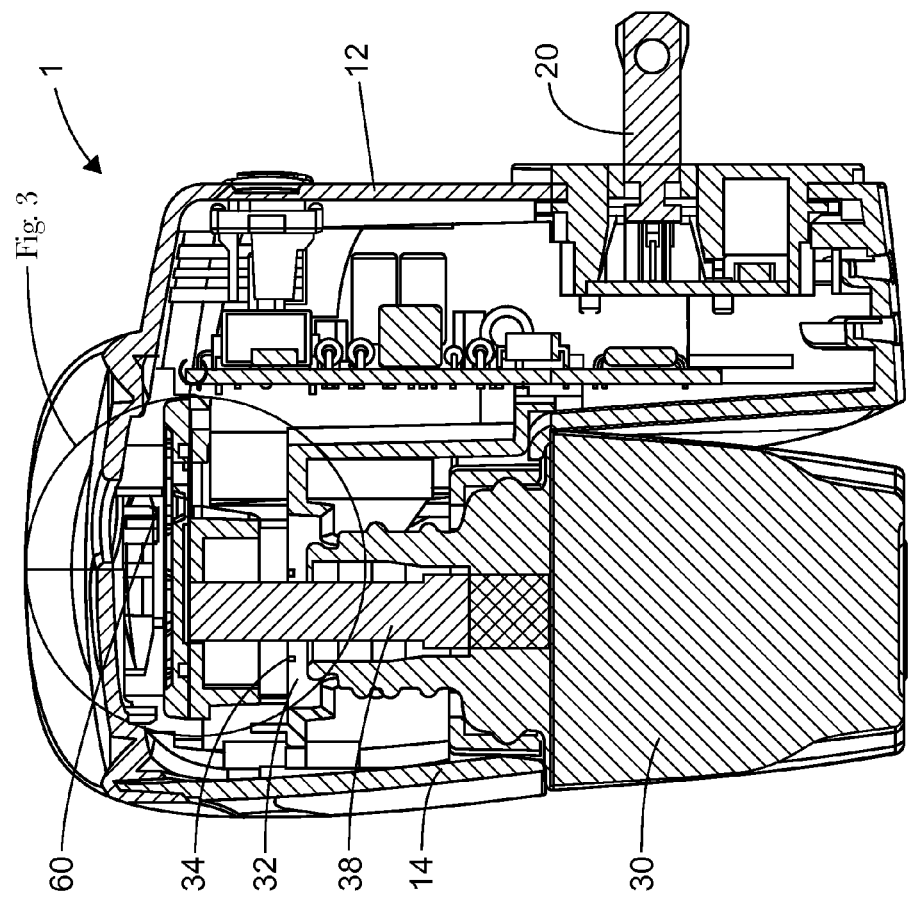
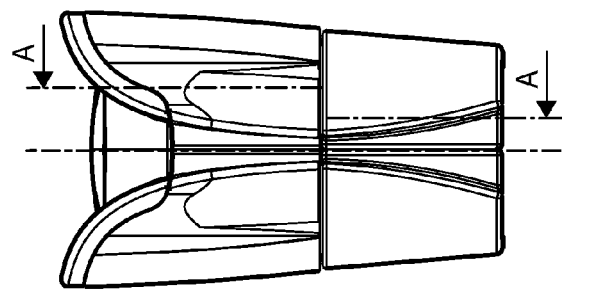

VOLATILE EMITTER WITH REDUCED SURFACE DEPOSITION AND IMPROVED SCENT NOTICEABILITY

CROSS REFERENCE TO RELATED APPLICATION

This application is a Continuation of U.S. application Ser. No. 12/123,704, filed May 20, 2008 now U.S. Pat. No. 8,135,265.

FIELD OF THE INVENTION

The present invention relates to a device for emitting volatile compositions, while reducing surface deposition and improving scent noticeability, and methods thereof. In some embodiments, the invention relates to a plug-in air freshener that includes a de-coupled piezoelectric actuator for emitting perfume compositions, and methods thereof.

BACKGROUND OF THE INVENTION

It is generally known to use an electrical device to evaporate a perfume and/or fragrance composition into a space, particularly a domestic space, such as a living room, to provide a pleasant aroma. There are a variety of such devices on sale, for example, AIRWICK® Diffuser ACTIF® (manufactured by Reckitt Benckiser), RENUZIT® Triscents (manufactured by Dial Corp.), or AMBI-PUR® fragrance diffuser (manufactured by Sara Lee). Generally, these devices consist of a perfume or fragrance source, an electrical heater, a capillary element or substrate from which the perfume is vaporized by application of heat, and a power supply. This arrangement provides a continuous supply of the perfume to the space in which the device is placed. However, it may take longer to fragrance a room, because this arrangement relies on vaporization involving the generation of smaller molecules that diffuse quickly and are more easily absorbed into surrounding objects.

One effort to address these problems is described in U.S. Pat. No. 6,752,327, Martens et al. The Martens patent discloses a plug-in air freshener having a piezoelectric actuator that vibrates a tilted orifice plate to dispense perfumes. The device disclosed in the Marten patent includes a wick and a piezoelectric actuator which is physically coupled to an orifice plate. However, the coupled piezoelectric actuator may cause bimodal droplets of perfume which may still deposit on the adjacent wall surface even with the titled orifice plate and the upwardly extending protrusion positioned between the orifice plate and the adjacent wall surface. Bimodal droplets are droplets that have already passed through an emitting orifice and fall back onto the emitting orifice to be emitted into the atmosphere a second time, but this time without passing through the emitting orifice. A vibrating perforate plate coupled to a piezoelectric actuator can provide such bimodal droplets. Bimodal droplets that undergo such process are generally larger partly because they are not limited by the size of the perforations in the emitting orifice. In addition to surface deposition, the tilted, coupled piezoelectric actuator device disclosed in Martens does not appear to address the problem that some liquid perfumes fall back onto the plate and flow forward, leaking down openings of the housing or off of the device and onto the floor or surrounding surfaces. Furthermore, when the device in Martens is not activated, a background level of perfume continues to be evaporated into the atmosphere. This effect causes the well-known phenomenon of scent habituation or olfactory fatigue.

The device described in WO 2007/062698A1, Hess et al., attempts to solve the deposition problem by utilizing a decoupled piezoelectric system. The Hess reference discloses a volatile liquid droplet dispenser device having a decoupled piezoelectric actuator positioned eccentric to the wick. However, the device described in Hess may still cause some deposition on surrounding surfaces. Therefore, there remains a continuing need for an improved device for fragrancing larger areas, while reducing surface deposition and improving noticeability of a fragrance over time.

SUMMARY OF THE INVENTION

The present invention relates to a device for emitting a volatile composition comprising: a housing having an x-direction, a y-direction perpendicular to said x-direction, a horizontal x-y plane defined by said x-direction and said y-direction, a z-direction perpendicular to said x-y plane; at least one volatile composition; at least one container for containing said at least one volatile composition; a capillary element positioned at least partially within said container; a channel in fluid communication with said capillary element an emitting orifice positioned upstream of said channel, said emitting orifice having a forward tilt from about +5 degrees to less than about +90 degrees; and a decoupled piezoelectric actuator for emitting said volatile composition through said emitting orifice.

The present invention also relates to a device for emitting a volatile composition comprising: at least one volatile composition; at least one container for containing said at least one volatile composition; a capillary element having an average porosity of about 20 microns to about 70 microns; a seal for supporting said capillary element, said seal comprising at least one vent hole having an average diameter of about 0.05 mm; at least one channel in fluid communication with said capillary element, said channel having an average diameter of about 10 microns and a length of about 10 mm; a reservoir positioned upstream from said channel; and an emitting orifice proximate to said reservoir; and a decoupled piezoelectric actuator for emitting said volatile composition through said emitting orifice.

The present invention also relates to methods of controlling surface deposition and improving scent noticeability by providing the above stated device.

BRIEF DESCRIPTION OF THE DRAWINGS

While the specification concludes with the claims particularly pointing and distinctly claiming the invention, it is believed that the present invention will be better understood from the following description taken in conjunction with the accompanying drawings in which:

FIG. 2a is a front plan view thereof;

FIG. 2b is a cross-sectional view thereof, taken along lines A-A in FIG. 2a;

DETAILED DESCRIPTION OF THE INVENTION

Figure 1:
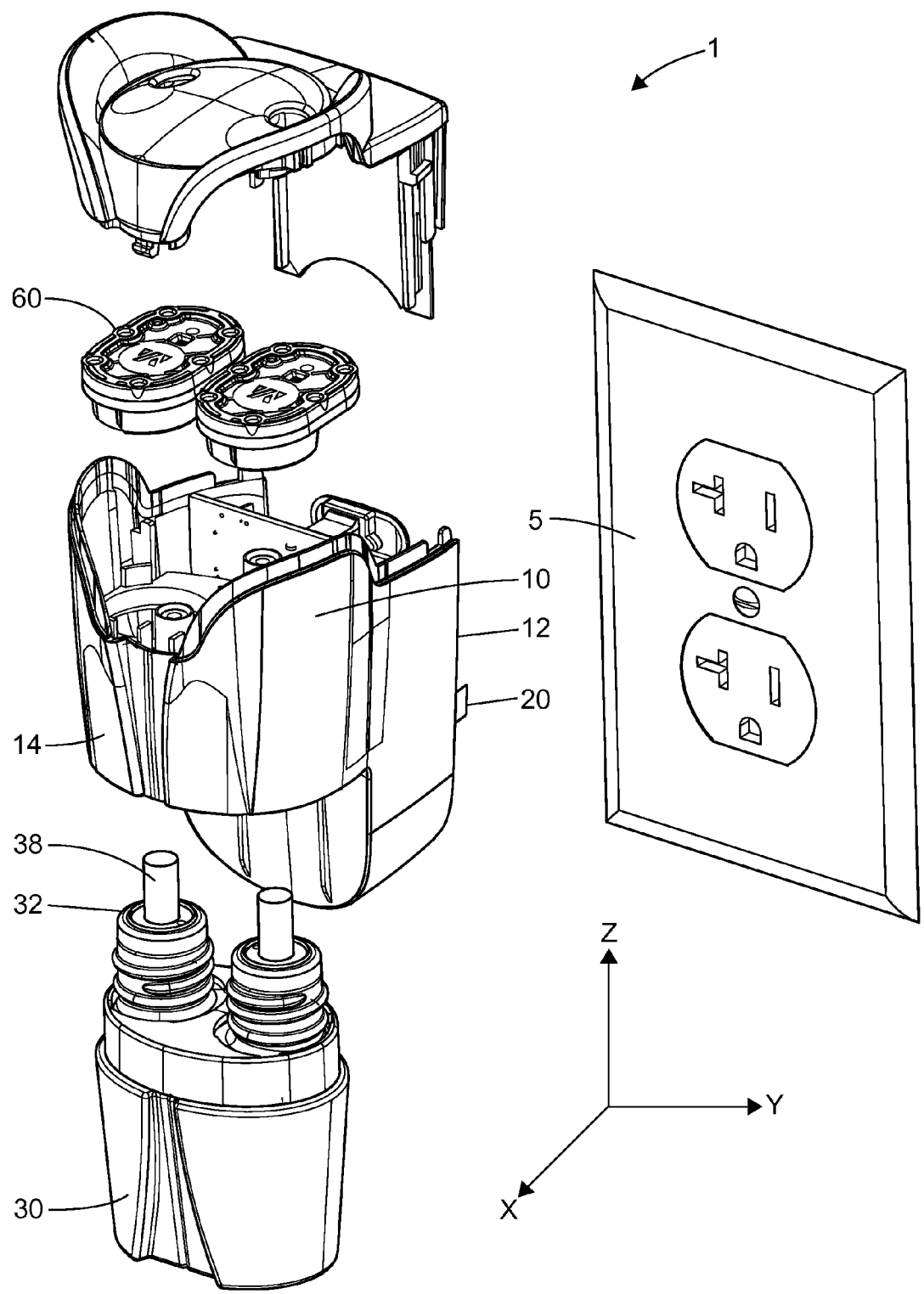
FIG. 1 is an exploded view of one embodiment of a device according to the present invention, illustrating the x-y-z directions.

The present invention relates to the above described device for emitting a volatile composition, while reducing surface deposition and improving noticeability of a fragrance over time.

"Decoupled piezoelectric", as used herein, means that the piezoelectric actuator is not directly attached to an emitting orifice or perforate plate from which a liquid containing a volatile composition is emitted into the atmosphere. Further, a decoupled piezoelectric actuator does not vibrate the emitting orifice to cause emission of liquid droplets from a device. Rather, a de-coupled piezoelectric actuator vibrates the liquid to be dispensed from a device and forces the liquid out through an adjacent emitting orifice or perforate plate. One decoupled piezoelectric actuator arrangement is described in WO 2007/062698.

"Unimodal droplets", as used herein, means droplets of volatile compositions that are emitted from a device by passing through a liquid outlet means plate. The droplet size distribution of unimoidal droplets is predetermined by the perforations of the liquid outlet means. Unimodal droplets do not include droplets that have already passed through an emitting orifice, such as a vibrating perforate plate, and fall back onto the top of the emitting orifice to be emitted into the atmosphere a second time; these droplets are considered bimodal. Without wishing to be bound by theory, it is believed that a device having unimodal droplets reduces surrounding surface deposition because the size distribution of unimodal droplets are controlled by the perforations in the emitting orifice or perforate plate.

"Volatile composition", as used herein, refers to a material or a discrete unit comprised of one or more materials that is vaporizable. The term "volatile composition", thus, includes but is not limited to compositions that are comprised entirely of a single volatile material. It is not necessary for all of the component materials of the volatile composition to be volatile. The terms "volatile material", "fragrance", and "scent" as used herein, include, but are not limited to pleasant or savory smells, and, thus, also encompass materials that function as insecticides, air fresheners, deodorants, aromacology material, aromatherapy material, or any other material that acts to condition, modify, or otherwise charge the atmosphere or to modify the environment.

In the case of multiple scented materials or fragrances, the different scented materials can be similar, related, complementary, or contrasting. It may not be desirable, however, for the scented materials to be too similar if the different scented materials are being used in an attempt to avoid the problem of scent habituation. Otherwise, the people experiencing the scents may not notice that a different scent is being emitted. The different scents can be related to each other by a common theme, or in some other manner. For example, the different scents can all be floral, fruit scents, etc. An example of scents that are different, but complementary might be a vanilla scent and a French vanilla scent.

Now referring to FIG. 1, the device 1 comprises a housing 10 supported on a power source 5, which may be an electrical wall outlet, by a plug 20 that is at least indirectly joined to the housing 10. In some embodiments, the plug 20 can be a car adapter for plugging into a cigarette lighter source in an automobile, a USB adapter for plugging into a USB port on a computer. In another embodiment, the power source 5 may be batteries.

The housing 10 has a front surface 12 and a rear 14 surface. The housing 10 also has an x-direction, which is the direction towards the front 12 surface and opposite or away from the power source 5. The housing 10 also has a y-direction perpendicular to said x-direction and a horizontal x-y plane defined by said x-direction and said y-direction, a z-direction perpendicular to said x-y plane.

The device 1 further comprises at least one container 30. The container 30 contains at least one volatile composition. It is possible for a single container to hold more than one type of volatile composition. Such a container could, for instance, have two or more compartments for volatile materials. In the embodiment shown in FIG. 1, the container 30 comprises two separate compartments. In some embodiments, there may be a plurality of containers each containing a volatile composition. The housing 10 may serve as a holder for the container 30 and any of the other components of the device 1 described below.

The container 30 can be made of any suitable material for containing a volatile composition. Suitable materials for the containers include, but are not limited to, glass and plastic. The container 30 may be part of the housing 10, or it may be separate components that are releasably connected to a portion of the device 1 such as the housing 10.

The container 30 may comprise a capillary element 38 for dispensing the volatile material. The capillary element 38 may be any commercially available wicking material such as a fibrous or porous wick that contains multiple interconnected open cells which form capillary passages to draw a volatile composition up from the container 30. In one embodiment, the capillary element 38 may be a high density wick composition to aid in the containment of the scent or odor of the volatile composition. As used herein, high density wick compositions include any conventional wick material known in the art having a pore diameter ranging from about 20 microns to about 70 microns, alternatively from about 30 microns to about 60 microns, alternatively from about 30 microns to about 50 microns, alternatively, about 40 microns to about 50 microns. Non-limiting examples of suitable compositions include polyethylene, polypropylene, ethyl vinyl acetate, polyether sulfone, polyvinylidene fluoride, polytetrafluroethylene, polyethersulfone, and mixtures thereof. U.S. Application No. 60/937,134 discloses capillary elements suitable for the present invention.

As seen in FIG. 2, the capillary element 38 may be at least partially in the container 30. In some embodiments, the capillary element 38 may be completely surrounded by the walls of the container 30. In such embodiments, the channel 50 may be partially within the container 30 to provide fluid communication with the capillary element 38. In one embodiment, the capillary element 38 is vertically aligned with the container 30. Depending upon the configuration of container 30, channel 50, and emitting orifice 60, a volatile composition may travel up or down the capillary element 38. In the embodiment shown in FIG. 2, the volatile composition travels through the capillary element 38 in an upward motion.

The device 1 and/or the container 30 may further comprise a seal 32 for supporting the capillary element 38. The seal 32 may have at least one vent hole 34 having an average diameter of about 0.05 mm. This arrangement may aid in containing the odor or scent of the volatile composition in the container 30 while still allowing atmospheric equilibrium to draw the volatile composition from the container 30 via capillary forces. The container 30 may also include a cap for covering the capillary element 38 when the container is not connected to the housing 10 or in use to release the volatile material therein.

Figure 3:
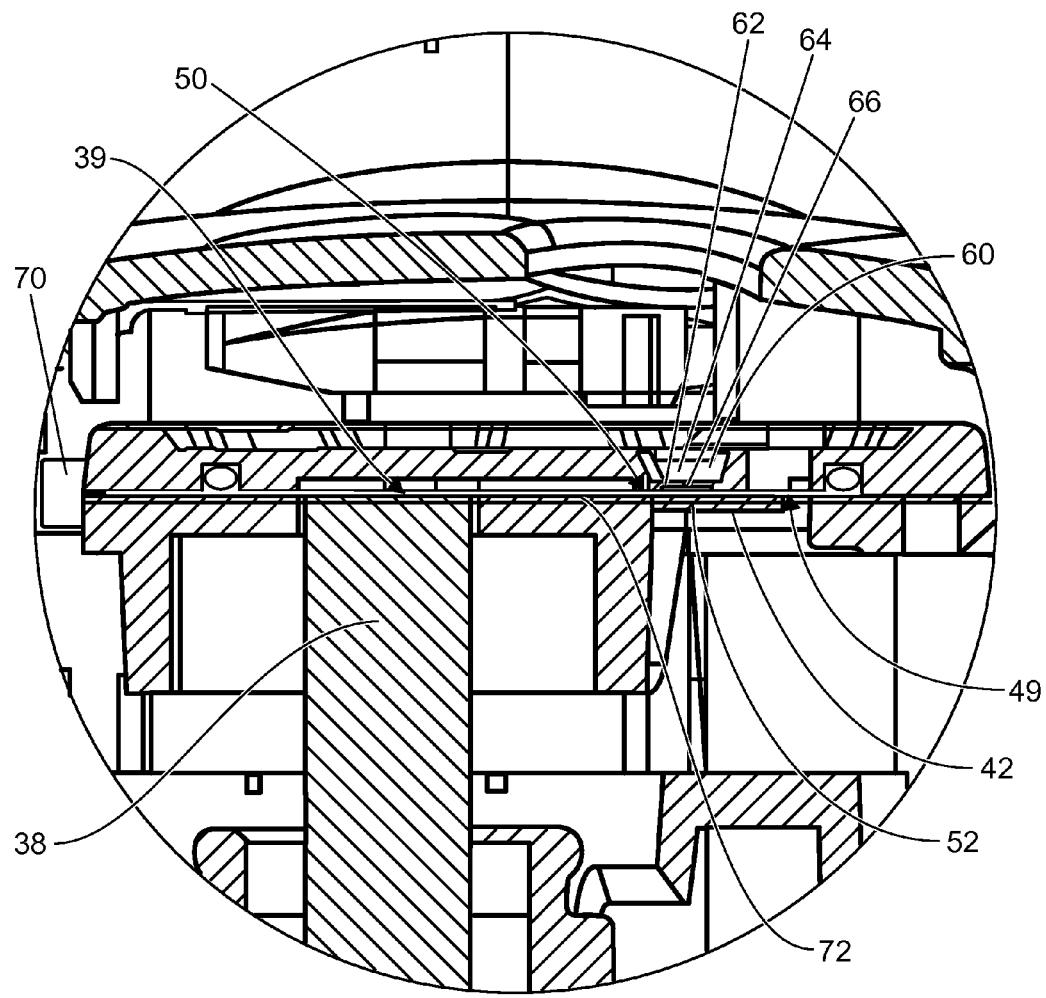
FIG. 3 is an enlarged cross-sectional view of the flow path in which the volatile composition travels to exit a device.

Referring to FIG. 3, the device 1 may include a channel 50 that may draw the volatile composition via capillary forces. The channel may extend laterally from the capillary element 38. The channel 50 may include a proximal 39 and distal 49 end. The distal end 49 may include a reservoir 52 In one embodiment, the length of the channel 50, measured from the capillary element 38 to center of the reservoir 52, is about 12 mm, alternatively about 13 mm, alternatively, about 14 mm, alternatively about 15 mm, alternatively about 11 mm, alternatively about 10 mm. In one embodiment, the opening of the channel 50 at the narrowest portion is about 10 microns, alternatively about 11 microns, alternatively about 12 microns, alternatively about 9 microns, alternatively about 8 microns. The opening of the channel 50 at the center of the reservoir 52 may be about 10 microns to about 150 microns, alternatively about 50 microns to about 150 microns, alternatively about 75 to 100 microns, alternatively about 85 microns to about 100 microns, alternatively about 90 microns to about 100 microns, alternatively about 95 microns to about 100 microns, alternatively about 100 microns.

After flowing through the channel 50, the volatile composition may then continue traveling upstream to a reservoir 52. The reservoir 52 may be about 10 mm in diameter. Adjacent to the reservoir 52 is a piezoelectric actuator 42. The reservoir 52 is also proximate to an emitting orifice 60. The piezoelectric actuator 42 is oriented to drive the volatile composition out of the channel 50 through an emitting orifice 60 and into the atmosphere. In one embodiment, the piezoelectric actuator is positioned below the reservoir, opposite the emitting orifice 60.

The emitting orifice 60 may comprise a plate having perforations 66 that are sized and distributed according to the desired droplet distribution. In one embodiment, the emitting orifice 60 is a perforated metal plate having perforations with an average pore size of about 10 microns to about 15 microns, alternatively about 12 microns to about 15 microns, alternatively about 15 microns. The plate may have a dimension of about 3 mm to about 3 mm. In another embodiment, the perforations 66 are about 10 microns to about 15 microns at the fluid inlet side 62 and from 4 to 5 microns at the fluid outlet side 64. Perforate plates suitable for the present invention are disclosed in U.S. Ser. No. 11/273,461 and WO2007/062698.

The emitting orifice 60 and the piezoelectric actuator 42 are decoupled from one another. The decoupling of the emitting orifice 60 from the piezoelectric actuator 42 limits the generation of droplet particle sizes to those that result from the pore size or sizes of the emitting orifice 60. In one embodiment, the emitting orifice 60 may be stationary even during vibration of the piezoelectric actuator 42.

Figure 4:
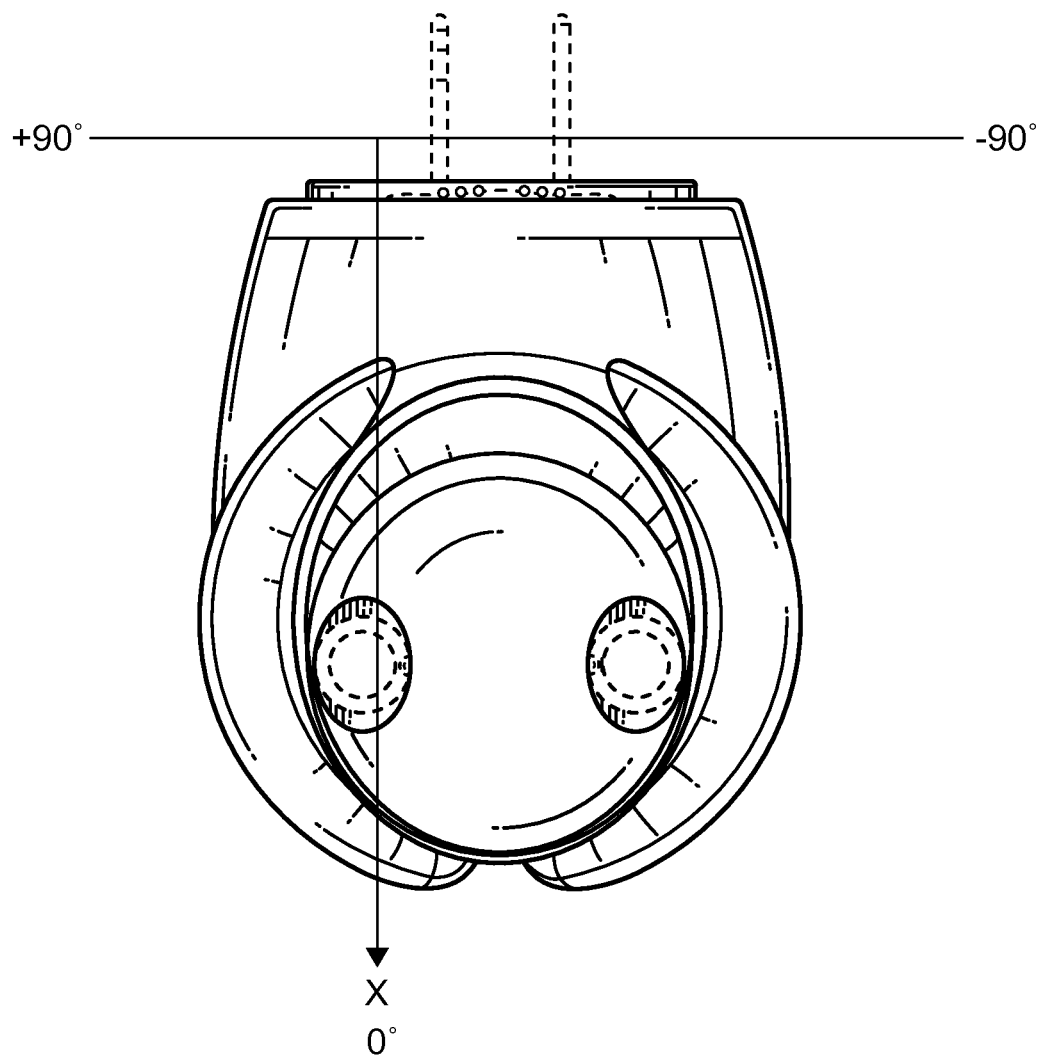
FIG. 4 is a top plan view of one embodiment a device according to the present invention, illustrating one parameter of the forward tilt angle as measured from the x-direction.
Figure 5:
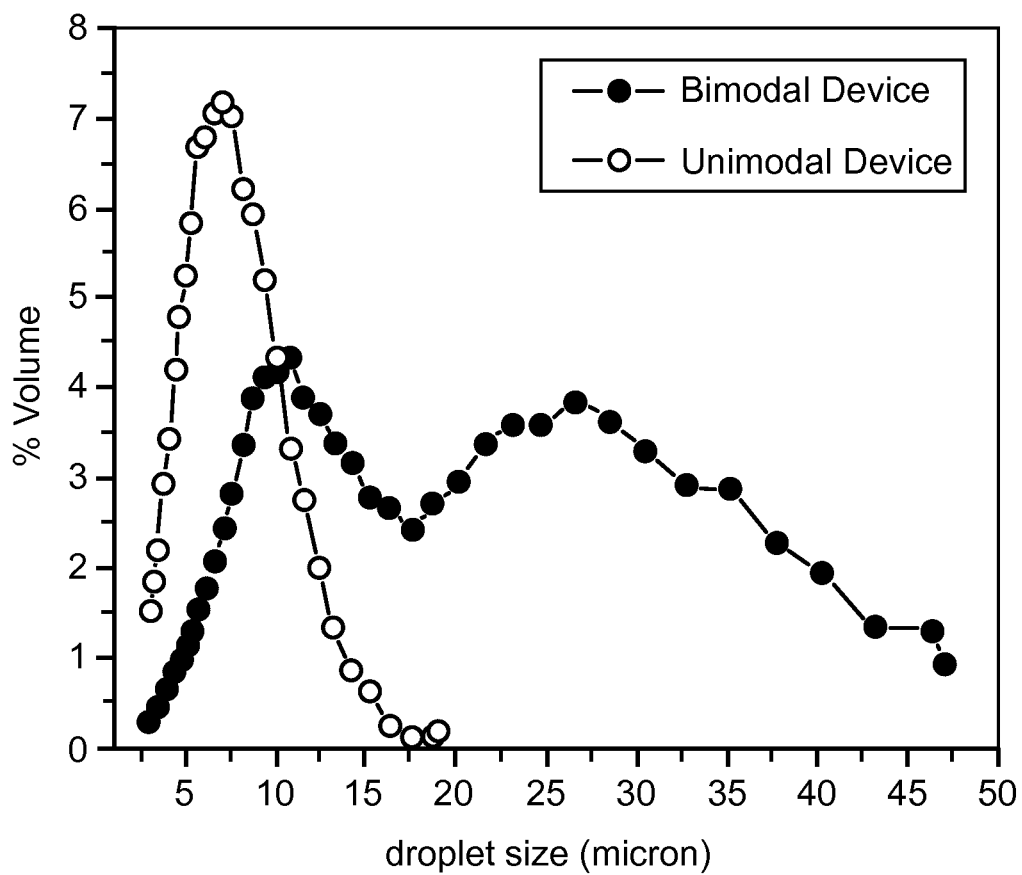
FIG. 5 is a graph illustrating the droplet size distribution of volatile compositions generated by bimodal or coupled piezoelectric devices and unimodal or decoupled piezoelectric devices with equal sized emitting orifices.

The emitting orifice 60 may have a forward tilt. This allows the device to eject the volatile composition at an angle to the x-y plane of the housing 10. The x-y plane of the housing 10 may intercept the center of the emitting orifice 60. For example, as shown in FIG. 1, where the device 1 is to be mounted on a power source 5 such as a wall outlet, the ejected liquid droplets of a volatile composition should be directed away from the wall so that they do not collect and damage the wall surface. This problem is overcome by orienting the emitting orifice 60 so that its x-y plane is tilted forward from the horizontal and away from nearby walls or other rearward surfaces. Forward tilt, as used herein, means an angle that satisfies both of the following parameters: (1) tilted towards the x-direction of the housing 1 at an angle from greater than about 0 degrees to less than about +90 degrees measured from the x-y plane; and (2) angled from 0 to +90 degrees or 0 to −90 degrees from the x-direction. The second parameter is best seen in FIG. 4. In one embodiment, the forward tilt is from about +5 degrees to about +90 degrees; alternatively, from about +5 to about +24 degrees; alternatively, from about +5 degrees to about +12 degrees, alternatively, from about +5 degrees to about +9 degrees; alternatively, alternatively, from about +7 degrees to about +9 degrees; alternatively, about +7 degrees; alternatively, about +9 degrees.

In one embodiment of the present invention, surface deposition may be further reduced by utilizing a drive means that operates at from about 160 to about 180 kHz; alternatively about 160 kHz; alternatively, about 180 kHz. A typical resonance frequency for a decoupled piezoelectric actuator may be about 80 kHz of the piezoelectric actuator 42.

The arrangement of the device 1 may improve scent noticeability by containing the odor of the volatile composition during times when the volatile composition is not intended to be emitted, such as rest periods where a piezoelectric actuator is not being actuated. Containment of a volatile composition may be measured by the amount of weight loss due to passive evaporation. Effective devices provide a passive evaporation weight loss of less than about 0.5 mg/hr for a given volatile composition. At this level of weight loss, the gas phase concentration of the volatile is below the odor detection threshold ("ODT") of most fragrances, which may be less than about 0.5 ppm for a given volatile composition. The effective reduction of the gas phase concentration below the ODT provides a deprivation state for the user.

In one embodiment, the device 1 comprises periods of emission in which the piezoelectric actuator 42 generates droplets of volatile compositions from the device 1; and periods of rest in which the piezoelectric actuator 42 is not generating droplets of volatile composition from the device 1. The rest period may be from about 15 minutes to about 30 minutes; and about 2 minutes where exposure is 30 minutes or less when using with fragrances having an ODT. During the rest period, the channel 50 may hinder vaporization of the volatile composition because it provides some distance between the capillary element 38 and the emitting orifice 60. The periods of rest may be beneficial in embodiments containing more than one perfume, because it may result in a cleaner, more noticeable presentation of the perfumes. This arrangement may also be beneficial when dealing with a limited supply of energy, such as in the case of a battery operated device.

Improved perfume intensity may also be noticed through improved particle size distribution of the volatile composition. Better control of intensity profiles may allow rapid changes between periods of high intensity and almost zero intensity. This fast exchange between periods of high intensity and zero intensity may increase the user perception of the high intensity periods and, in this way, achieve a more noticeable intensity profile. This scheme may not be achievable by slower reacting systems, such as heater systems or coupled piezoelectric systems. Coupled piezoelectric systems may have poor control on particle size or inefficient containment of volatile compositions such that the larger particle can linger longer than expected creating less clear sensorial profiles between the emissions period and the rest period.

Optional Features

Where there is more than one volatile composition, the device 1 may further comprise a switching mechanism that changes the volatile material being emitted by the device 1. The switching mechanism controls the activation of the piezoelectric element 42. The switching mechanism can comprise any suitable type of mechanism that causes the device to change the volatile material being emitted. One type of switching mechanism is described in U.S. Pat. No. 7,223,361.

The device 1 may also include a heating element 70. Without wishing to be bound by theory, it is believed that small changes in temperature reduce the viscosity of a volatile composition containing fluid which may, in turn, increase the plume height and flow rate of the fluid. In one embodiment, at least a portion of the channel 50 is enclosed by a steel plate 72 which is heated by a heating element 70. The heating element 70 can be positioned adjacent to the steel plate 72 and/or the reservoir 52 to improve the emitting performance of the device 1. Heat from the heating element 70 can be generated by known means in the art. For example, resistors may be secured adjacent to the channel 50 by the housing 10 or directly connected to the steel plate 72 on the channel 50 using any commercially available heat conductive adhesive. One heat conductive adhesive is TRA-BOND 2151 two-part, epoxy made by TRA-CON. The heat will be distributed by means of thermal conduction. The temperature of the steel plate 72 may be controlled. One such way to do this would be by means of a thermistor, which is a type of resistor with resistance varying according to its temperature, used in conjunction with a microcontroller already present in the device 1. Effective temperatures are from about 18° C. to about 29° C.

The device 1 may also include an electronic circuit that allows the piezoelectric actuator 42 to operate using a square wave function. Square waves have been shown to increase the both flow rate and plume height of piezoelectric devices. Square waves are generated by means of what is commonly called by those skilled in the art of electrical engineering as an "H-bridge". Square waves are believed to be better suited for plug-in devices over battery powered devices for various reasons. For example, H-bridges can only generate an AC wave form with a peak to peak voltage of two times the voltage supplied to the H-bridge, which may not be sufficient to drive a piezoelectric actuator without the use of other discrete electrical components. Therefore, for a battery powered device to produce a square wave of 120 volts peak to peak, the H-bridge would have to be supplied with 60 volts DC. This may require the use of a DC to DC converter to step up the voltage level provided by the batteries to 60 volts DC. This is believed to be inefficient and may reduce battery life. This is easily overcome in a plug-in device wherein the H-Bridge in the plug in is supplied with the rectified wall voltage of about 110 to 120 volts and resulting in an input voltage to the H-Bridge of approximately 155 to 170 volts. This voltage can be further adjusted, if necessary, by a simple voltage divider. With this arrangement, a plug-in application could have the benefit of higher plume height and flow rate that is achieved from driving the piezoelectric actuator with a square wave using basic electronic components.

The device 1 may comprise a number of additional optional features. The device 1 may include indicators so that a person is further made aware that the volatile material being emitted has changed. Such indicators can be visual and/or audible. For example, in the case of scented materials, such an indicator may allow a person to see which scent is being emitted at a given time. The indicators may be in the form of lights. In another example, at least a portion of the device 1 (such as all or a portion of the housing) or the containers may be made of a type of plastic that changes color when heated.

The device 1 may also include an "on/off" switch to allow a user to turn the device on and off without removing it from the electrical socket. The device can be provided with a control that allows the user to control the emission period of the volatile materials, and/or the time between the emission of the different volatile materials, or the time that the volatile materials are emitted during an overlapping time period. For example, in one non-limiting embodiment, if the device is provided with the capability of emitting each volatile material during a period greater than 15 minutes and less than or equal to 24 hours, then the device can be provided with a control that allows the user to set the emission period to 72 minutes, or to one hour, for example.

The device 1 may also include a remote control that allows the user to control any, or all, of the emission properties of the device 1 (including, but not limited to changing the volatile material being emitted) without touching the device 1.

The device 1 may comprise a microprocessor that has less component parts compared to analog circuits, and improved circuit quality from lot to lot. The microprocessor can allow the user to program and control the temperature profile by modulation to alter performance. If desired, the microprocessor may be connected to a user interface. This can be any suitable type of user interface. Examples of types of user interfaces include, but are not limited to LCD screens and LED's. In addition, the microprocessor enables components to allow multiple devices (such as those located in different parts of a room, or in different rooms), to communicate with each other. For example, the microprocessor can enable a remote control to send digital signals via an infrared beam to turn another device "on" or "off".

In some embodiments, the device 1 can be configured to turn on and off in response to some stimulus, such as by sensors that respond to light, noise and/or motion. For example, one of the devices can be set up to turn on when it senses light, and another device can be set to turn off when it senses light. In another example, a microprocessor can be used with motion sensors to turn on the device 1 (for example, a heater and/or a fan in the device). For example, the device 1 can be off all the time until a person moves in the vicinity of the motion sensor. The device 1 can then turn on when a person walks in the vicinity of the motion sensor. Using a microprocessor provides flexibility in controlling the characteristics of the emission of the volatile materials. This is because it is possible to replace the microprocessor if it is desired to change the emission characteristics. Replacing the microprocessor eliminates the need to modify the entire circuit.

The following example is for illustrative purposes only and does not limit the full scope of the invention as defined by the claims.

EXAMPLE I

A device having a decoupled piezoelectric actuator, in accordance with the present invention, is utilized with a single container that contains 30 ml of air freshening composition. The container contains a high density wick that is fluidly connected to a lateral channel with an emitting orifice. The emitting orifice has a forward tilt angle of +7 degrees when measured from the x-y plane of the housing. The channel includes a steel plate which is heated to about 29° C. upon the device being plugged into a power source. The channel also includes an emitting orifice having perforations with an average pore size of about 4.1 microns. The assembled apparatus includes drive electronics for dispensing approximately 35 mg of air freshening composition every hour upon receiving power from an electrical wall outlet. The device is plugged into the electrical wall outlet approx 20 cm from the table top surface. The center of the emitting orifice is 3 cm from the nearest point on the adjacent wall surface. The device is left to operate on the electrical wall outlet for a period of 17 hours to 18 hours. The deposition, flow rate, and plume height of the air freshening composition are measured.

Deposition is determined by collecting the non-volatilized or re-deposited liquid air freshening compositions that have deposited on the table top surface, approximately 20 cm below the emitting orifice, on three filter papers: Whatman 40 (Ashless, 18.5 cm Catalog number—1440 185). Two of filter papers are placed under the bottom front edge of the device. Another filter paper is used to measure the deposition at the adjacent wall surface, 3 cm above the device. The third filter paper is cut to fit the top of the device and placed with the hole cut out over the center of the device. Filter papers are extracted using 5 ml of an internal standard solvent solution containing 11.4 mg of C14 in 250 ml of methanol. All samples are analyzed by injecting 1 microliter onto a 6890/5973 GC/MS with a DB-1 column (1 μm film thickness, 0.32 mm ID, 60 m length). Quantitative results are calculated by referencing to a known standard. The data are reported as μg of material and graded according the following scale: 0 rating equal <5 μg; 1=from 5 μg to 10 μg; 2=from 10 μg to 20 μg; 3=from 20 μg to 50 μg; 4=>50 μg.

Flow rates are measured as weight loss over time. The weight of the device is measured using a Mettler Toledo Excellence Xs403S response 0.001 g over time and the weight difference (in mg) was divided by the time period in hours to give a flow rate in mg/hr.

Plume height is determined by placing the device into the center of a cylindrical chamber. At the rear of the chamber, behind the device, a darkened screen is provided. A ruler is positioned so that the zero cm mark is directly in line with the top of the device. The vertical distance of the plume is measured by a ruler and the average plume height, in cm, is taken from five consecutive sprays.

Droplet-size distributions are measured using an Oxford Laser Visisizer System. This technique uses high-speed, high-resolution digital photography to acquire images of the spray. The laser light is diffused and used as a backlight (not a beam); the sample volume is approximately 1 $mm^3$. These images are then analyzed by the Visisizer software to yield a droplet size distribution. The measured distributions appear rougher than distributions measured with other techniques (such as laser diffraction) since this method actually counts and sizes individual particles. Relevant spray statistics are then calculated from the raw droplet-size data. In most cases, at least 2000 droplets are used to calculate the statistics.

Table 1 demonstrates that overall deposition is best when the emitting orifice has a forward tilt between +7 to +24 degrees from the x-y plane of the housing.

TABLE 1

| Forward Tilt Angle | Wall Deposition | Surface Deposition | Housing Deposition |
|---|---|---|---|
| 0 to +2 | 3 | 0 | 1 |
| +5 | 3 | 0 | 2 |
| +7 | 1 | 0 | 1 |
| +9 | 0 | 0 | 1 |
| +12 | 1 | 0 | 1 |
| +24 | 0 | 0 | 0 |
| +38 | 0 | 1 | 0 |
| +45 | 0 | 1 | 0 |
| +52 | 0 | 1 | 0 |
| +60 | 0 | 2 | 1 |
| +90 | 0 | 2 | 1 |

Table 2 shows that heat improves the flow rate of the volatile composition in the channel.

TABLE 2

| Surface Temperature (° C.) | Flow Rate (mg/hr) |
|---|---|
| 18 | 8 |
| 24 | 19 |
| 29 | 34 |

Table 3 shows the effect of vibrational frequency of the decoupled piezoelectric actuator on plume height as it moves from an operational resonance frequency, to an anti-resonance frequency (or no resonance), and then to a second operational resonance frequency (double the first operational frequency). It is generally known that coupled piezoelectric systems emit volatile compositions within a single or very narrow frequency range, in the order of about 80 kHz. It is not completely understood why a decoupled piezoelectric device operates differently, yet surprising that such device emits volatile composition at a broad range of 160-220 kHz. It is also surprising that the plume height is two times the plume height generated via the first operational resonance frequency.

TABLE 3

| Frequency (kHz) | Plume height (cm) |
|---|---|
| 80 | 6 |
| 100 | 8 |
| 120 | 10 |
| 140 | <5 |
| | Anti-resonance |
| 160 | 14 |
| 180 | 16 |
| 200 | 10 |
| 220 | <5 |

EXAMPLE II

The following four devices are tested for containment of ethyl 2-methyl butyrate (E2MB), a highly volatile material, as well as a commercially available volatile composition (VC 1). Each device contains 10 ml of ethyl 2-methyl butyrate. Each device is placed in a room with an approximate volume of 8,150 lt at ambient condition with an average temperature of 25° C. The flow rate is measured using the procedure described above for five consecutive days and reported as mg/hr. This measurement and the volume of the room is used to calculate the gas phase concentration in parts per billions (ppb).

TABLE 4

| Device/System | Non activated emission (mg/hr) for E2MB | Non activated emission (mg/hr) for VC 1 | Concentration in a 8,150 lt space (ppb) for VC 1 |
|---|---|---|---|
| Commercially available electrical heater only device | 50 | 2.50 | 1000 |
| Coupled Piezoelectric Device | 6.5 | 0.75 | 938 |
| Decoupled piezoelectric device of Example I but with a +5° Tilt angle | 2.5 | 0.20 | 250 |
| Decoupled piezoelectric device of Example I but with a +10° Tilt angle | 2.2 | 0.18 | 225 |

Table 4 demonstrates that a decoupled piezoelectric device according to the present invention contains the commercially available volatile composition well below 500 ppb; this is better than the results achieved by a traditional electrical heater device or a coupled piezoelectric device. Many volatile materials have an ODT higher than 250 ppb. Thus, the present invention may achieve ODT below the uncontained ODT of these volatile compositions. This may assist with achieving a deprivation state.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A device for emitting a volatile composition comprising:
    a housing having an x-direction, a y-direction perpendicular to said x-direction, a horizontal x-y plane defined by said x-direction and said y-direction, a z-direction perpendicular to said x-y plane;
    at least one volatile composition;
    at least one container for containing said at least one volatile composition;
    a capillary element positioned at least partially within said container;
    a channel in fluid communication with said capillary element;
    an emitting orifice positioned upstream from said channel, said emitting orifice having a forward tilt from about +5 degrees to less than about +90 degrees; and
    a decoupled piezoelectric actuator for emitting said volatile composition through said emitting orifice.

2. The device of claim 1 wherein said forward tilt is from about +5 degrees to about +24 degrees.

3. The device of claim 1 wherein said forward tilt is from about +5 degrees to about +9 degrees.

4. The device of claim 1 wherein said forward tilt is about +9 degrees.

5. The device of claim 1 wherein said capillary element and said channel are a single piece construction.

6. The device of claim 1 wherein said decoupled piezoelectric actuator is driven at about 160 kHz to about 180 kHz.

7. The device of claim 1 wherein said device further comprises a heating element electrically connected to said plug and oriented proximate to said channel.

8. The device of claim 1 wherein said at least one volatile composition is an air freshener.

9. The device of claim 1 wherein said volatile composition is emitted for a first time period followed by a second time period having no emission.

10. The device of claim 9 wherein said first time period is from about 4 hours to less than about 8 hours in length, and said second time period is from about 15 minutes to about 45 minutes.

11. The device of claim 9 wherein said first time period is about 15 minutes and said second time period is about 2 minutes.

12. The device of claim 9 wherein said second time period is about 25% of said first time period.

13. A method of improving scent noticeability comprising the steps of providing the device of claim 9.

14. A device for emitting an air freshening composition comprising:
    a housing having an x-direction, a y-direction perpendicular to said x-direction, a horizontal x-y plane defined by the x-direction and the y-direction;
    a plug for at least indirectly supporting said housing on an electrical wall outlet;
    at least one volatile air freshening composition;
    at least one container for containing said at least one volatile air freshening composition, said container is releasably connected to said housing;
    a wick positioned at least partially within said container;
    a lateral channel in fluid communication with said wick;
    a reservoir positioned upstream from said channel;
    an emitting orifice proximate said reservoir, said emitting orifice having a forward tilt from about +5 degrees to less than about +90 degrees; and
    a decoupled piezoelectric actuator for emitting a volatile composition through said emitting orifice, said decoupled piezoelectric actuator is driven at about 160 kHz to about 180 kHz.

15. A device for emitting a volatile composition comprising:
    at least one volatile composition;
    at least one container for containing said at least one volatile composition;
    a capillary element having an average porosity of about 20 microns to about 70 microns;
    a seal for supporting said capillary element, said seal comprising at least one vent hole having an average diameter of about 0.05 mm;
    at least one channel in fluid communication with said capillary element, said channel having an average diameter of about 10 microns and a length of about 10 mm;
    a reservoir positioned upstream from said channel;
    an emitting orifice proximate to said reservoir, wherein said emitting orifice is positioned upstream from said at least one channel and wherein said emitting orifice has a forward tilt from about +9 degrees to about +52 degrees; and
    a decoupled piezoelectric actuator for emitting said volatile composition through said emitting orifice.

16. The device of claim 10 wherein said capillary element has an average porosity of about 40 microns to about 50 microns.

17. The device of claim 15, wherein said volatile composition is emitted for a first time period followed by a second time period, said second time period having a passive evaporation weight loss of less than about 0.5 mg/hr.

18. A method of improving scent noticeability comprising the steps of providing the device of claim 15.

* * * * *